US00PP34547P2

(12) United States Plant Patent
van Dijk

(10) Patent No.: US PP34,547 P2
(45) Date of Patent: Sep. 6, 2022

(54) ***HYDRANGEA* PLANT NAMED 'HISHA'**

(50) Latin Name: *Hydrangea macrophylla*
Varietal Denomination: HISHA

(71) Applicant: Roy Robin van Dijk, De Lier (NL)

(72) Inventor: Roy Robin van Dijk, De Lier (NL)

(73) Assignee: HI BREEDING B.V., DeLier (NL)

( * ) Notice: Subject to any disclaimer, the term of this patent is extended or adjusted under 35 U.S.C. 154(b) by 0 days.

(21) Appl. No.: 17/676,741

(22) Filed: Feb. 21, 2022

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan McCormick Ewoldt
(74) *Attorney, Agent, or Firm* — C. Anne Whealy

(57) ABSTRACT

A new and distinct cultivar of *Hydrangea* plant named 'HISHA', characterized by its upright and broadly spreading plant habit; freely branching habit; strong and sturdy greyed purple-colored stems; freely flowering habit; large and dense inflorescences with dark purplish pink-colored sterile flowers; and good post-production longevity.

2 Drawing Sheets

Figure 1:
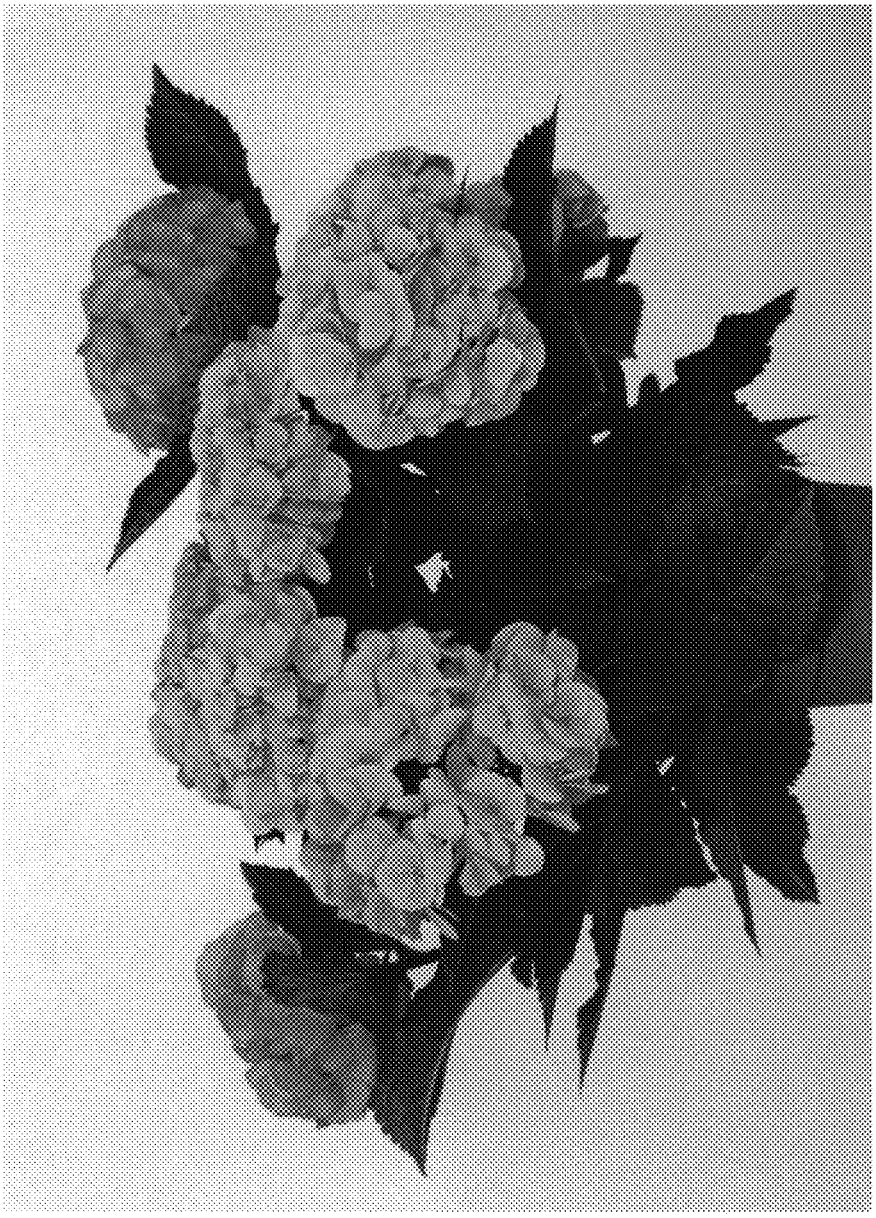

Botanical designation: *Hydrangea macrophylla.*
Cultivar denomination: 'HISHA'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'HISHA'.

The new *Hydrangea* plant is a product of a planned breeding program conducted by the Inventor in De Lier, The Netherlands. The objective of the breeding program is to create new sturdy and strong *Hydrangea* plants with attractive inflorescences and good postproduction longevity.

The new *Hydrangea* plant originated from a cross-pollination on Apr. 15, 2015 of a proprietary selection of *Hydrangea macrophylla* identified as code number 1342, not patented, as the female, or seed, parent with a proprietary selection of *Hydrangea macrophylla* identified as code number 1213, not patented, as the male, or pollen, parent. The new *Hydrangea* plant was discovered and selected as a single flowering plant from within the progeny of the stated cross-pollination in a controlled greenhouse environment in De Lier, The Netherlands on Apr. 4, 2017.

Asexual reproduction of the new *Hydrangea* plant by terminal vegetative cuttings since Jun. 11, 2017 in a controlled greenhouse environment in De Lier, The Netherlands has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HISHA'. These characteristics in combination distinguish 'HISHA' as a new and distinct *Hydrangea* plant:

1. Upright and broadly spreading plant habit.
2. Freely branching habit.
3. Strong and sturdy greyed purple-colored stems.
4. Freely flowering habit.
5. Large and dense inflorescences with dark purplish pink-colored sterile flowers.
6. Good post-production longevity.

Plants of the new *Hydrangea* can be compared to plants of the female parent selection. Plants of the new *Hydrangea* differ primarily from plants of the female parent selection in the following characteristics:

1. Stems of plants of the new *Hydrangea* are sturdier than stems of plants of the female parent selection.
2. Plants of the new *Hydrangea* have better postproduction longevity than plants of the female parent selection.

Plants of the new *Hydrangea* can be compared to plants of the male parent selection. Plants of the new *Hydrangea* differ primarily from plants of the male parent selection in stem strength as stems of plants of the new *Hydrangea* are sturdier than stems of plants of the male parent selection. In addition, stems of plants of the new *Hydrangea* are greyed purple in color whereas stems of plants of the male parent selection are green in color.

Plants of the new *Hydrangea* can also be compared to plants of *Hydrangea macrophylla* 'HBA 202911', not patented. In side-by-side comparisons, plants of the new *Hydrangea* differ primarily from plants of 'HBA 202911' in the following characteristics:

1. Plants of the new *Hydrangea* are more vigorous than plants of 'HBA 202911'.
2. Stems of plants of the new *Hydrangea* are sturdier than stems of plants of 'HBA 202911'.
3. Stems of plants of the new *Hydrangea* are greyed purple in color whereas stems of plants of 'HBA 202911' are green in color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet (FIG. 1) is a side perspective view of a typical flowering plant of 'HISHA' grown in a container.

Figure 2:
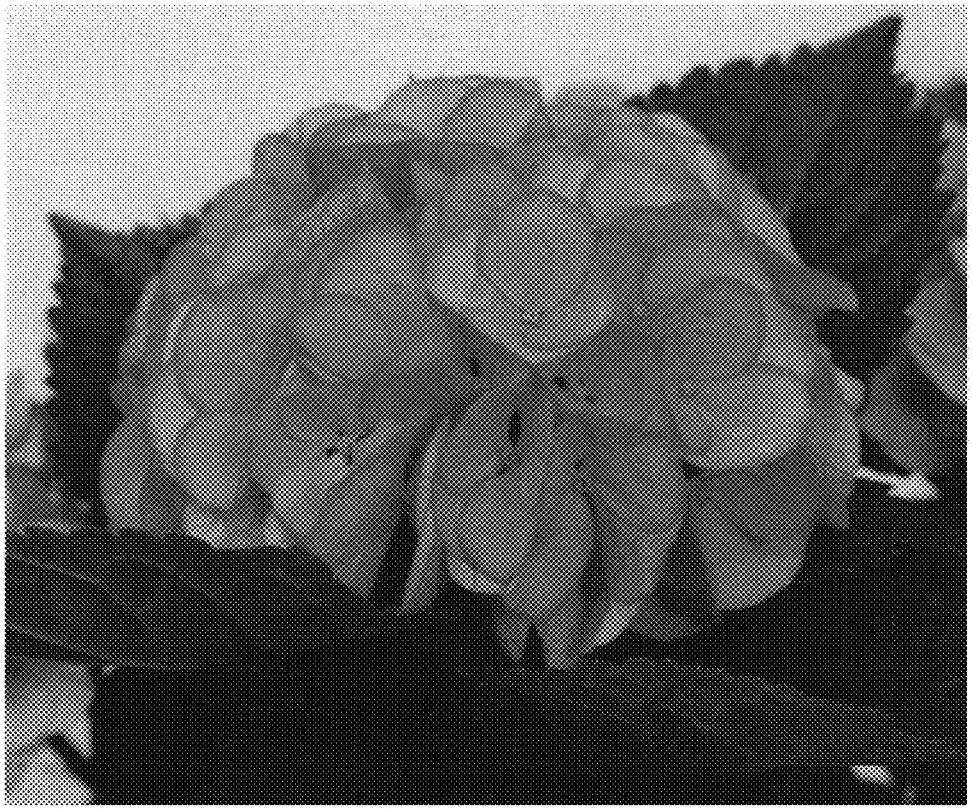

The photograph at the top of the second sheet (FIG. 2) is a close-up view of a typical inflorescence of 'HISHA'.

Figure 3:
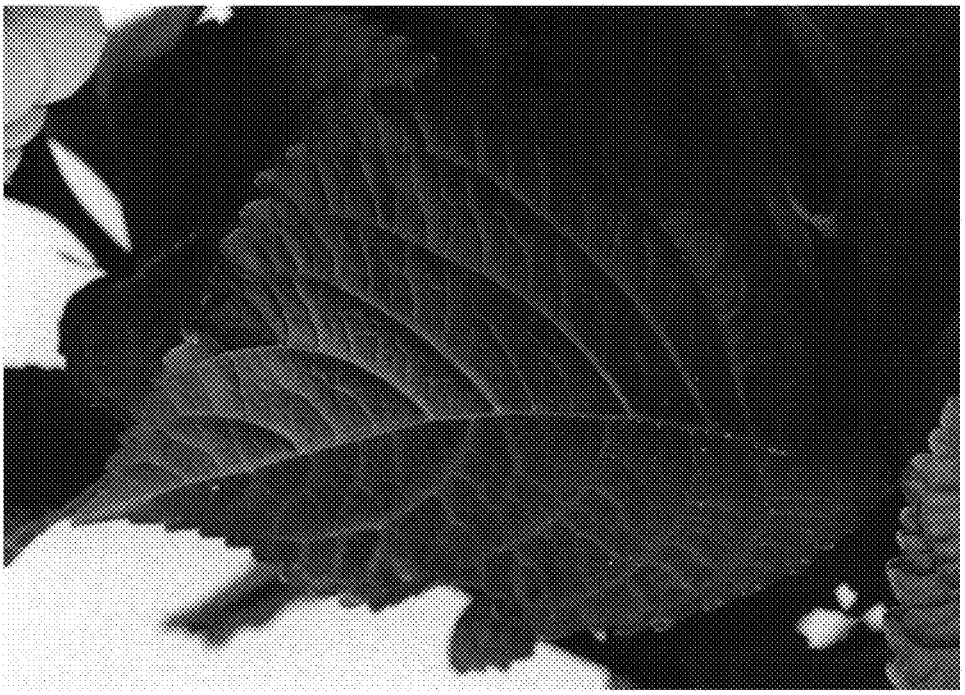

The photograph at the bottom of the second sheet (FIG. 3) is a close-up view of a typical leaf of 'HISHA'.

DETAILED BOTANICAL DESCRIPTION

Plants used in the aforementioned photographs and in the following description were grown during the late winter and early spring in 14-cm containers in a glass-covered greenhouse in De Lier, The Netherlands and under cultural practices typical of commercial *Hydrangea* production. During the production of the plants, day temperatures ranged from 20° C. to 35° C., night temperatures ranged from 10° C. to 22° C. and light levels averaged 4,000 lux. Plants of the new *Hydrangea* were pinched one time and were 18 months old when the photographs and description were taken. In the following description, color references are made to The Royal Horticultural Society Colour Chart, 2015 Edition, except where general terms of ordinary dictionary significance are used. Plants have not been evaluated when treated with aluminum sulfate (or "blued").

Botanical description: *Hydrangea macrophylla* 'HISHA'.

Parentage:

*Female, or seed, patent*.—Proprietary selection of *Hydrangea macrophylla* identified as code number 1342, not patented.

*Male, or pollen, patent*.—Proprietary selection of *Hydrangea macrophylla* identified as code number 1213, not patented.

Propagation:

*Type cutting*.—By vegetative terminal cuttings.

*Time to initiate roots, summer*.—About twelve days at temperatures about 22° C.

*Time to initiate roots, winter*.—About two weeks at temperatures about 20° C.

*Time to produce a rooted young plant, summer*.—About four weeks at temperatures about 22° C.

*Time to produce a rooted young plant, winter*.—About one month at temperatures about 19° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Upright, broadly outwardly spreading and mounding plant habit; flattened globular in overall shape; strong and sturdy stems; moderately vigorous growth habit and moderate growth rate; about six months from propagation are required to produce small finished flowering plants.

*Plant height*.—About 33.7 cm.

*Plant diameter or area of spread*.—About 57.3 cm.

Lateral branch description:

*Branching habit*.—Freely branching habit with about twelve lateral branches per plant; pinching enhances lateral branch development.

*Length*.—About 21.1 cm.

*Diameter*.—About 7 mm.

*Internode length*.—About 5 cm.

*Strength*.—Strong, sturdy.

*Aspect*.—About 50° from vertical.

*Texture*.—When developing, moderately pubescent; developed, smooth, glabrous; and fully developed, woody.

*Color, developing*.—Close to 187A.

*Color, fully developed*.—Darker than N186D; when woody, close to 199A to 199D.

Leaf description:

*Arrangement*.—Opposite, simple.

*Length*.—About 13.2 cm.

*Width*.—About 10.2 cm.

*Shape*.—Broadly ovate to broadly elliptic.

*Apex*.—Broadly apiculate.

*Base*.—Short attenuate.

*Margin*.—Coarsely crenate to serrate.

*Texture, upper surface*.—Slightly rugose, glabrous.

*Texture, lower surface*.—Moderately rugose, glabrous.

*Venation pattern*.—Pinnate.

*Color*.—Developing leaves, upper surface: Close to 137A. Developing leaves, lower surface: Close to 146B. Fully developed leaves, upper surface: Darker than a blend of 139A and 147A; venation, close to 146A to 146B. Fully developed leaves, lower surface: Close to a blend of 147B and 191A; venation, mostly close to 147B and towards the petiole, close to 183A.

*Petioles*.—Length: About 2.4 cm. Diameter: About 4.5 mm. Texture and luster, upper surface: Smooth, glabrous; slightly glossy. Texture and luster, lower surface: Smooth, glabrous; moderately glossy. Color, upper surface: Close to 145A; at the edges, close to a blend of 183A and 200B. Color, lower surface: Close to 183A with proximal end, close to 144B.

Flower description:

*Flower type and habit*.—Showy rotate sterile flowers and small, inconspicuous rotate fertile flowers arranged on mophead-type terminal panicles;

panicles flattened globular in shape; sterile flowers face upright to outwardly and fertile flowers mostly upright.

*Fragrance*.—None detected.

*Natural flowering season*.—In the garden, plants flower continuously from the late spring to late summer in The Netherlands; flower dormancy can be broken by giving a cold treatment.

*Flower longevity*.—Good postproduction longevity; sterile flowers maintain good substance for about six weeks on the plant, sterile flowers persistent; fertile flowers last for a few days on the plant, fertile flowers not persistent.

*Quantity of flowers*.—Freely flowering habit; about 80 sterile flowers per panicle and about 55 fertile flowers per panicle.

*Panicle height*.—About 9 cm.

*Panicle diameter*.—About 15.3 cm.

*Panicle peduncles*.—Length: About 3 cm. Diameter: About 3 mm. Strength: Strong. Aspect: Primary peduncles, mostly erect; lateral peduncles, about 45° from primary peduncle axis. Texture: Densely pubescent. Color: Close to 183C.

*Sterile flower buds*.—Length: About 6 mm. Diameter: About 1.1 cm. Shape: Irregular and broadly cup-shaped. Color: Close to 150D; at the apex, close to 62A.

*Fertile flower buds*.—Length: About 3 mm. Diameter: About 3.5 mm. Shape: Flattened globular. Color: Close to 63C and 182D.

*Sterile flower diameter*.—About 3 cm to 4.9 cm.

*Sterile flower depth* (*height*).—About 1.2 cm to 1.9 cm.

*Fertile flower diameter*.—About 8 mm.

*Fertile flower depth* (*height*).—About 5 mm.

*Petals, sterile flowers*.—Quantity and arrangement: Four, or occasionally five, in a single whorl. Length: About 2.5 mm. Width: About 1.8 mm. Shape: Ovate, concave. Apex: Acute. Base: Cuneate. Margin: Entire. Texture and luster, upper and lower surfaces: Smooth, glabrous; matte. Color: When opening and fully opened, upper surface: Close to 70B; color does not change with subsequent development. When opening and fully opened, lower surface: Close to 64C; color does not change with subsequent development.

*Petals, fertile flowers*.—Quantity and arrangement: Five, or occasionally six, in a single whorl. Length: About 3.5 mm. Width: About 2.25 mm. Shape: Ovate, concave. Apex: Acute. Base: Cuneate. Margin: Entire. Texture and luster, upper and lower surfaces: Smooth, glabrous; matte. Color: When opening, upper surface: Close to 70B. When opening, lower surface: Close to 64C. Fully opened, upper surface: Close to 70B; color does not change with subsequent development. Fully opened, lower surface: Close to 64C and towards the apex, close to N66D; color does not change with subsequent development.

*Sepals, sterile flowers*.—Quantity and arrangement: Typically four, or occasionally three or five, in a single whorl; imbricate. Length: About 1.8 cm to 2.7 cm. Width: About 2.3 cm to 3.7 cm. Shape: Reniform to rhomboidal, slightly concave. Apex: Broadly and bluntly acute to obtuse. Base: Broadly cuneate to truncate. Margin: Entire; coarsely undulate. Texture and luster, upper and lower surfaces: Smooth, glabrous; matte. Color: When opening, upper surface: Close to 61C; towards the apex, close to 67C; at the margins, close to N66A. When opening, lower surface: Close to 68A; towards the apex, close to 68B; at the margins, close to N66B with veins, close to 67A. Fully opened, upper surface: Close to 68A; towards the margins, close to 68B; towards the apex and at the margin edges, close to 67B; with subsequent development, colors becoming closer to 68B to 68C, towards the margins, close to 68C to 68D, and towards the apex and at the margin edges, close to 67B to 67C. Fully opened, lower surface: Close to 68B; at the margins, close to 67B; with subsequent development, colors becoming closer to 68B to 68C with margin edges, close to 67B.

*Sepals, fertile flowers*.—Quantity and arrangement: Five in a single whorl. Length: About 1.5 mm. Width: About 1 mm. Shape: Broadly ovate to deltoid. Apex: Acute. Base: Cuneate. Margin: Entire. Texture and luster, upper and lower surfaces: Smooth, glabrous; matte. Color: When opening and fully opened, upper surface: Close to 58A; color does not change with subsequent development. When opening and fully opened, lower surface: Close to 63C to 63D; color does not change with subsequent development.

*Pedicels, sterile flowers*.—Length: About 2.2 cm. Diameter: About 1.5 mm. Strength: Moderately strong. Aspect: About 30° from main peduncle axis. Texture and luster: Densely pubescent; slightly glossy. Color: Close to a blend of 46A and 185A.

*Pedicels, fertile flowers*.—Length: About 6 mm. Diameter: About 1 mm. Strength: Moderately strong. Aspect: About 10° from vertical. Texture and luster: Densely pubescent; matte. Color: Close to 186B.

*Reproductive organs, sterile flowers*.—Stamens: Quantity per flower: Eight. Filament length: About 2.5 mm. Filament color: Close to 70A to 70B. Anther shape: Broadly oblong. Anther length: About 1 mm. Anther color: Close to 186C. Pollen amount: Moderate. Pollen color: Close to 155A. Pistils: Pistil quantity per flower: Two, or occasionally, three. Pistil length: About 1.5 mm. Stigma shape: Club-shaped. Stigma color: Close to 64B. Style length: About 1 mm. Style color: Close to 64D. Ovary color: Close to 64D.

*Reproductive organs, fertile flowers*.—Stamens: Quantity per flower: Ten. Filament length: About 2.5 mm. Filament color: Close to 64B to 64C. Anther shape: Broadly oblong. Anther length: About 1 mm. Anther color: Close to 186C. Pollen amount: Moderate. Pollen color: Close to 155A. Pistils: Pistil quantity per flower: Three. Pistil length: About 2 mm. Stigma shape: Club-shaped. Stigma color: Close to 64A. Style length: About 1.5 mm. Style color: Close to 70D. Ovary color: Close to 75A to 75B.

*Seeds*.—To date, seed development has not been observed on plants of the new *Hydrangea*.

Pathogen & pest resistance: To date, plants of the new *Hydrangea* have not been observed to be resistant to pathogens and pests common to *Hydrangea* plants.

Temperature tolerance: Plants of the new *Hydrangea* have been shown to be suitable for USDA Hardiness Zones 5 through 9.

It is claimed:

1. A new and distinct *Hydrangea* plant named 'HISHA' as illustrated and described.

* * * * *